United States Patent
Staley

(10) Patent No.: US 6,777,213 B2
(45) Date of Patent: Aug. 17, 2004

(54) ISOLATION OF CARBOXYLIC ACIDS FROM FERMENTATION BROTH

(75) Inventor: Michael D. Staley, Cincinnati, OH (US)

(73) Assignee: Cognis Corporation, Cincinnati, OH (US)

( * ) Notice: Subject to any disclaimer, the term of this patent is extended or adjusted under 35 U.S.C. 154(b) by 0 days.

(21) Appl. No.: 10/640,239

(22) Filed: Aug. 13, 2003

(65) Prior Publication Data

US 2004/0082042 A1 Apr. 29, 2004

Related U.S. Application Data

(60) Provisional application No. 60/421,922, filed on Oct. 29, 2002.

(51) Int. Cl.[7] .............................. C12P 7/46; C12P 7/48; C12P 7/62; C12P 7/64; C07C 51/43
(52) U.S. Cl. ...................... 435/134; 435/136; 435/137; 435/142; 435/145; 435/146; 554/70; 554/169; 554/206; 554/207; 562/494; 562/580; 562/582; 562/584; 562/589; 562/590; 562/592
(58) Field of Search ................................ 435/134, 136, 435/137, 142, 145, 146; 554/70, 109, 206, 207; 562/494, 582, 584, 589, 590, 592; 652/580

(56) References Cited

U.S. PATENT DOCUMENTS

| | | | |
|---|---|---|---|
| 2,450,858 A | 10/1948 | Fitzpatrick et al. | |
| 2,813,113 A | 11/1957 | Goebel et al. | |
| 4,275,011 A | * 6/1981 | Tanaka et al. | 435/134 |
| 4,606,863 A | 8/1986 | Nakazawa et al. | |
| 4,627,192 A | 12/1986 | Fick | |
| 5,254,466 A | 10/1993 | Picataggio et al. | |
| 5,273,898 A | * 12/1993 | Ishii | 435/198 |
| 5,380,928 A | 1/1995 | Malek et al. | |
| 5,420,316 A | 5/1995 | Rebrovic | |
| 6,232,480 B1 | * 5/2001 | Kinsman et al. | 554/147 |
| 6,331,420 B1 | 12/2001 | Wilson et al. | |
| 6,376,223 B1 | * 4/2002 | Staley | 435/136 |
| 6,455,715 B1 | * 9/2002 | Frische et al. | 554/112 |
| 6,660,505 B2 | * 12/2003 | Staley | 435/136 |

FOREIGN PATENT DOCUMENTS

| | | |
|---|---|---|
| JP | 0183639 | 3/1989 |
| WO | WO 94/10122 | 5/1994 |
| WO | WO 00/20566 | 4/2000 |

OTHER PUBLICATIONS

Foglia et al., "Oxidation of Unsaturated Fatty Acids with Ruthenium and Osmium Tetroxide", J. Am. Oil Chem. Soc., Nov. 1977, vol. 54, pp. 870A–872A.

Foglia et al., "Oxidation of Alkenes with Use of Phase Transfer Catalysis[1]", J. Am. Oil Chem. Soc., Nov. 1977, vol. 54, pp. 858A–861A.

Practices of Am. Oil Chem. Soc., 5th ed. ISBN: 0–935315–97–7, AOCS Press (Book).

* cited by examiner

Primary Examiner—Herbert J. Lilling
(74) Attorney, Agent, or Firm—Aaron R. Ettelman; Steven J. Trzaska

(57) ABSTRACT

A process for recovering carboxylic acids from an aqueous mixture such as a fermentation broth using a solvent containing at least one olefin without the need for first removing the spent microorganism cells is provided. A co-solvent which increases the partition coefficient of the solvent relative to the carboxylic acid may optionally be included. The resulting carboxylic acid is hydrogenated to produce a saturated carboxylic acid.

38 Claims, No Drawings

ISOLATION OF CARBOXYLIC ACIDS FROM FERMENTATION BROTH

BACKGROUND OF THE INVENTION

This application claims the benefit of copending provisional application serial No. 60/421,922 filed on Oct. 29, 2002.

STATEMENT REGARDING FEDERALLY SPONSORED RESEARCH OR DEVELOPMENT

This invention was funded, at least in part, under a grant from the Department of Commerce, NIST-ATP Project Number 98-05-0013. The Government may therefore have certain rights in the invention.

FIELD OF THE INVENTION

This invention relates to a process for recovering a carboxylic acid from an aqueous media such as a fermentation broth. The carboxylic acid is made by the biological oxidation of a substrate by a microorganism.

DESCRIPTION OF RELATED ART

Standard methods for recovering carboxylic acids in general, and polycarboxylic acids in particular, from fermentation broths are typically based on the physical separation of the spent microorganism cells from the aqueous phase, such as by centrifugation, followed by precipitation of the carboxylic acid as a result of pH reduction of the aqueous phase. This method is unsatisfactory for a number of reasons, the most notable of which includes the problem of physically separating the spent cells and then acidifying the cell-free broth to effect the precipitation of the carboxylic acid. The precipitation of the carboxylic acid is time consuming and the separation and isolation of the precipitated carboxylic acid is not always clean, i.e., there can be impurities which adversely affect the quality and purity of the final product.

Accordingly, there is a continuing need for improved processes for recovering carboxylic acids from a fermentation broth.

SUMMARY OF THE INVENTION

The present invention involves an improved process for the recovery of a carboxylic acid made by the biological oxidation of a substrate by a microorganism such as a yeast. Carboxylic acids are recovered from a fermentation broth by extracting the broth with a solvent containing one or more olefins without the need for first removing the spent microorganism cells. In one aspect, a cosolvent is combined with one or more olefins to create a solvent which favorably adjusts the partition coefficient. A preferred solvent for the extraction of carboxylic acids from a fermentation broth contains a mixture of tertiary-butyl acetate and diisobutylene.

In another aspect, a method for isolating at least one carboxylic acid from an aqueous mixture is provided which includes providing an aqueous mixture containing at least one carboxylic acid, contacting a solvent containing at least one olefin with the aqueous mixture, allowing the at least one carboxylic acid to separate into a solvent, isolating the solvent containing the at least one carboxylic acid from the aqueous mixture, separating the solvent from the at least one carboxylic acid, and hydrogenating the at least one carboxylic acid to produce a saturated carboxylic acid. A co-solvent may be combined with the at least one olefin.

Solvents are provided which, in one embodiment, include a mixture of a minority amount of tertiary butyl acetate and a majority amount of diisobutylene. During the process of recovering the carboxylic acids, one or more co-solvents may be included which generally aid in the process, e.g., by reducing the amount of solvent needed to remove the carboxylic acids, and/or the number of extraction cycles necessary to adequately remove the carboxylic acids from the fermentation broth.

After employing a fermentation procedure to produce a carboxylic acid, the viscosity of the fermentation broth may optionally be adjusted, preferably by heating the fermentation broth, to form a flowable liquid. The pH of a fermentation broth which contains one or more carboxylic acids may be optionally adjusted to a value of from at least about 2.0 to about 7.0. The carboxylic acid-containing broth is contacted with a solvent containing one or more olefins to extract the carboxylic acid. The carboxylic acid may then be isolated by separating crystals of the carboxylic acid from the extraction solvent. Means for isolating the carboxylic acid from the extraction solvent are known to those skilled in the art and include, but are not limited to, evaporation, distillation, melt crystallization, and crystallization. The resulting carboxylic acid may then be further purified by distillation and/or processed by hydrogenation to saturate any unsaturated carboxylic acids.

DETAILED DESCRIPTION OF THE INVENTION

Except in the claims and the operating examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, throughout this description, unless expressly stated to the contrary: percent, "parts" of, and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description or of generation in situ by chemical reactions specified in the description, and does not necessarily preclude other chemical interactions among the constituents of a mixture once mixed; and the term "mole" and its grammatical variations may be applied to elemental, ionic, and any other chemical species defined by number and type of atoms present, as well as to compounds with well defined molecules.

It is understood that a carboxylic acid is any compound containing one or more carboxyl groups. A polycarboxylic acid is any compound having two or more carboxyl groups.

A suitable liquid extractant is a liquid organic solvent which is not miscible with the fermentation broth but in which the carboxylic acids to be recovered from the fermentation broth are soluble. The extractant is preferably chosen such that when cooled, the carboxylic acid will crystallize out of solution. Alternatively, an extractant is chosen that readily evaporates, leaving the carboxylic acid behind.

A flowable liquid is a fluid whose molecules are free to move past one another while remaining in sliding contact.

The process for the recovery of a carboxylic acid according to the present invention was based on fermenting a microorganism in a culture medium which is comprised of a nitrogen source and at least one organic substrate, and then recovering the carboxylic acid by contacting the broth with a suitable extractant. The organic substrate can be any compound which can be oxidized to a compound having at least one carboxyl group by biooxidation. For the production of carboxylic acids, the substrate can be any compound having at least one methyl group, a terminal carboxyl group and/or a terminal functional group which is oxidizable to a carboxyl group by is biooxidation. The substrate can also contain one or more carbon-carbon multiple bonds and/or one or more carboxylic or heterocyclic aromatic rings. The microorganism can be any microorganism that is capable of biologically oxidizing an organic substrate as set forth above to a compound having at least one carboxyl group.

The process for the recovery of a carboxylic acid is applicable to the production by fermentation of any carboxylic acid that has between 3 and 36 carbon atoms, preferably 5 to 36 atoms and more preferably 9 to 36 carbon atoms. The process for the recovery of a carboxylic acid is particularly applicable to the production of polycarboxylic acids by fermentation and most particularly to the production of dicarboxylic acids. Examples of such dicarboxylic acids include, but are not limited to, oxalic acid, maleic acid, succinic acid, glutaric acid, adipic acid, pimelic acid, phthalic acid, azelaic acid, sebacic acid, dodecanedioic acid, brassylic acid, 9-octadecenedioic acid, C-36 dimer acid and isomers thereof. The process is also applicable to the recovery of monobasic carboxylic acids which can be saturated, unsaturated or polyunsaturated. Examples of such monocarboxylic acids include, but are not limited to, caprylic, pelargonic, capric, undecylic, lauric, myristic, pentadecanoic, palmitic, heptadecanoic, stearic, arachidic, palmitoleic, oleic, erucic, linoleic, linolenic and isomers thereof.

The microorganisms can be any microorganism capable of biooxidizing the substrate as defined herein. Typically, such a microorganism will be a yeast. Several strains of yeast are known to excrete alpha, omega-dicarboxylic acids as a byproduct when cultured on alkanes or fatty acids as the carbon source. Certain strains are set forth, e.g., in U.S. Pat. Nos. 6,331,420 and 5,254,466, and International Application No. PCT/US99/20797, the entire contents of which are each incorporated by reference herein. Preferably, the microorganism is a beta-oxidation blocked C. tropicalis cell which has been genetically modified so that the chromosomal POX4A, POX4B and both POX5 genes have been disrupted. The substrate flow in this strain is redirected to the omega-oxidation pathway as the result of functional inactivation of the competing β-oxidation pathway by POX gene disruption. The strain may also have one or more reductase genes amplified which results in an increase in the amount of rate-limiting omega-hydroxylase through P450 gene amplification and an increase in the rate of substrate flow through the w-oxidation pathway. Such strains are discussed in detail in U.S. Pat. No. 6,331,420 and International Application No. PCT/US99/20797.

The process for making a dicarboxylic acid includes fermenting a suitable microorganism in a culture medium comprised of a nitrogen source, an organic substrate and a cosubstrate wherein the substrate is a compound having one carboxyl group and one methyl group or is a compound having one methyl group and a functional group that can be at least partially hydrolyzed to a carboxyl group and optionally wherein the substrate is partially neutralized. Saponification may be desirable for some raw materials.

Examples of suitable nitrogen sources are disclosed in U.S. Pat. No. 5,254,466 and International Application No. PCT/US99/20797. The cosubstrate can be any fermentable carbohydrate such as glucose, fructose, maltose, glycerol and sodium acetate. The preferred cosubstrate is glucose, preferably a liquid glucose syrup, for example, 95% dextrose-equivalent syrup, or even lower dextrose-equivalent syrups. Such materials contain small amounts of disaccharides, trisaccharides, and polysaccharides which can be hydrolyzed during the fermentation by the addition of an amylase enzyme.

The organic substrate can be any compound having at least one methyl group which can be biooxidized. One type of organic substrate includes alkanes having from 3 to 36 carbon atoms, preferably those having 9 to 36 carbons, examples of which include, but are not limited to, nonane, decane, undecane, dodecane, tridecane, tetradecane, pentadecane, hexadecane, heptadecane, octadecane, nonadecane, eicosane and their isomers. The organic substrate can also be any saturated aliphatic compound having at least one terminal methyl group, a terminal carboxyl group and/or a terminal functional group which is oxidizable to a carboxyl group by biooxidation. The organic substrate can also be any unsaturated aliphatic compound having at least one internal carbon-carbon double bond and at least one terminal methyl group, a terminal carboxyl group and/or a terminal functional group which is oxidizable to a carboxyl group by biooxidation. One suitable source of organic substrates is high oleic acid sunflower fatty acids (HOSFA) which are commercially available from Cognis Corp., Cincinnati, Ohio.

In those instances where the process according to the invention is applied to the production of dicarboxylic acids, the organic substrate is preferably any compound having one carboxyl group and one methyl group or is a compound having one methyl group and a functional group that can be at least partially hydrolyzed to a carboxyl group. Thus, the organic substrate in this case can be any aliphatic saturated or unsaturated monocarboxylic acid except formic acid and acrylic acid. Examples of carboxylic acid substrates include, but are not limited to: caprylic, pelargonic, capric, undecylic, lauric, myristic, pentadecanoic, palmitic, heptadecanoic, stearic, arachidic, palmitoleic, oleic, erucic, linoleic, linolenic, and isomers thereof.

The substrate can be optionally partially neutralized with a base, preferably an alkaline earth metal hydroxide prior to the addition of the substrate to the fermentation broth. Certain preferred hydroxides are calcium, magnesium, sodium and potassium hydroxide. While the organic substrate will preferably be a monocarboxylic acid for the production of polycarboxylic acids, it can be any compound having one carboxyl group and one methyl group or having one methyl group and a functional group thereby permitting at least partial neutralization of the carboxyl group formed in the hydrolysis. Particularly preferred monocarboxylic acids are oleic acid and pelargonic acid.

A process for the recovery of a carboxylic acid according to the present invention involves optionally adjusting the viscosity of the broth, preferably by heating the fermentation broth to form a flowable liquid. Adjusting the viscosity of the broth allows for better contact between the broth and the solvent containing one or more olefins that will be used for the extraction. This improves the effectiveness of the extraction. The preferred temperature of the broth is from about 0° C. to about 100° C., and more preferably from about 70° C. to about 80° C., with a temperature of about 75° C. being most preferred.

A preferred embodiment incorporates a pH of the fermentation broth in a slightly acidic pH range. An optional step of the process for the recovery of carboxylic acids following the fermentation process is the adjustment of the pH of the fermentation broth in the range from about 2.0 to about 7.0, preferably in the range from about 3.0 to about 6.0, and more preferably in the range from about 4.0 to about 6.0, with a pH of about 5.0 being most preferred. Typically, the pH value of the broth will fall in the range of from 5.0 to 7.5 but may be higher than 7.5 depending upon the fermentation conditions, the nature of the substrate, cosubstrate, the microorganism and the carboxylic acid formed in the fermentation. The pH adjustment takes place during or after the fermentation process. Typically, carboxylic acids recovered by the process are unsubstituted aliphatic carboxylic acids. These acids will normally have a pKa in the range of from about 4 to about 5. The acid used to adjust the pH should be a stronger acid than the carboxylic acid to be recovered from the fermentation broth, preferably a strong mineral acid. A strong carboxylic acid can also be used. Acids having a pKa less than that of the carboxylic acid to be recovered can be used. The stronger the acid, the lower the pKa value will be. Examples of acids used to adjust the pH include, but are not limited to, arsenic, hydrobromic, hydrochloric, chloric, iodic, nitric, nitrous, phosphoric, phosphorous, hypophosphorous, pyrophosphoric, sulfuric, sulfurous, thiosulfuric, tellurous, formic, chloroacetic, lactic, glycolic, citric and mixtures thereof.

The next step is to contact the fermentation broth with a suitable extraction solvent, i.e., a solvent containing one or more olefins. Olefins are well-known in the art.

Examples such as cyclohexene (commercially available from Uniroyal Chemical Company, Inc., Naugatuck, Conn.), 1-hexene (commercially available from Chevron Chemical Company, Cedar Bayou, Tex.), 1-octene (commercially available from Shell Chemical Company, Geismar, La.), 1-decene (commercially available from Amoco Corporation, Pasadena, Tex.), diisobutylene, (commercially available from Texas Petrochemicals Corporation Houston, Tex.), Nonene (nonlinear) (propylene trimer) (tripropylene) (commercially available from Arco Products Co., Carson, Calif.), NEODENE® (commercially available from Shell Chemical Company, Houston, Tex.) and NEOSOLV® (commercially available from Shell Chemical Company, Houston, Tex.) perform as extraction solvents for the extraction of carboxylic acids from a fermentation broth in accordance with the present invention. Petroleum distillates containing one or more olefins such as kerosene, Lacolene (available from Ashland Distribution Company, Columbus, Ohio) and Varnish Makers and Painter's (VM&P) Naptha (commercially available, e.g., from Ashland Distribution Company, Columbus, Ohio) are also suitable extraction solvents for the extraction of carboxylic acids from a fermentation broth. Where a petroleum distillate is used, the petroleum distillate must include an olefin and does not, for purposes of this disclosure, encompass petroleum distillates which lack an olefin such as, for example, petroleum ether and ligroin. Thus, suitable olefins are aliphatic or alicyclic hydrocarbons with one or more double bonds along the chain. Higher olefins may also be used and include those having chains of up to 20 or more carbon atoms and those that have a double bond between the first two carbons of the chain, which are known as alpha olefins, e.g., 1-decene or 1-dodecene.

At least one of the above-described extraction solvents are contacted with the fermentation broth for a time sufficient to extract carboxylic acids from the fermentation broth. Suitable time ranges are dependent upon the concentration of diacid in the broth, the viscosity of the broth, the temperature of the broth, and other factors normally taken into account by those skilled in the art. Typical extraction times may range, e.g., from about 0.5 seconds or less to about 2 minutes or more. For example, the extraction time can be 15 minutes or more. The amount of extraction solvent may also be varied by those skilled in the art and can range from about $\frac{1}{100}$ of the broth volume to about 10 times the broth volume or more.

One or more cosolvents may be added to adjust the partition coefficient of the extraction solvent thus reducing the amount of solvent and/or stages of extraction required to sufficiently remove carboxylic acids from a fermentation broth. For example, the partition coefficient of diisobutylene in combination with the fermentation media and techniques described herein is typically less than about 1, i.e., about 0.5. As used herein, the partition coefficient is the concentration of diacid in extraction solvent by weight over the concentration of diacid by weight in the aqueous phase at equilibriun. In the case of carboxylic acids having 16 to 20 carbon atoms, the partition coefficient may be adjusted upward to a preferred range of about 3 to about 5 by addition of a suitable cosolvent which modifies the partition coefficient. Those skilled in the art will recognize that cosolvents which increase polarity are suitable for producing such an adjustment. If the partition coefficient becomes too high, unwanted emulsion formation may occur as well as a loss in selectivity of the desired carboxylic acid. Routine experimentation by those skilled in the art may be utilized to determine the amount of cosolvent necessary to suitably adjust the partition coefficient. Suitable cosolvents include, but are not limited to, esters of fatty acids and alcohols such as tert-butyl acetate and pentyl acetate, fatty alcohols such as 1-octanol, 2-octanol, dodecanol and decanol, aliphatic long chain ketones such as 2-octanone and 2-decanone, other water insoluble ketones such as methyl isobutyl ketone, ethers such as methyl tert-butyl ether, esters of fatty alcohols such as methyl hexanate, methyl octanate, ethyl hexanate and ethyl octanate, and non-polar solvents such as chloroform, methyl chloride, toluene, benzene, xylene and the like.

A preferred extraction solvent for extraction of carboxylic acids from a fermentation broth is a mixture of diisobutylene as a solvent and tertiary butyl acetate as a cosolvent. Addition of tertiary butyl acetate to diisobutylene increases the partition coefficient of the solvent as compared to diisobutylene alone. In this embodiment, the amount of diisobutylene may range from about 5% to about 99% and the amount of tertiary butyl acetate may range from about 1% to about 95% by weight. Preferably, the solvent includes a mixture of a minority amount of tertiary butyl acetate and a majority amount of diisobutylene. A majority amount means that there is more diisobutylene than tertiary butyl acetate. In a preferred embodiment, the amount of diisobutylene is about 90% and the amount of tertiary butyl acetate is about 10% by weight. Some advantages of using a solvent herein with a partition coefficient which has been adjusted upwardly as described above include the following: (1) less emulsion formation during extraction; (2) lower concentrations of carboxylate salts and sulfur are present in this solvent than when other solvents such as 2-octanol and 2-octanone are utilized alone; (3) these solvents are more environmentally friendly than other solvents such as, for example, aromatic solvents; (4) diisobutylene and tertiary butyl acetate have similar boiling points which allows easier recycling of the solvent without altering its composition; and (5) fewer repetitions of the extraction process are needed to obtain suitably pure product.

The extraction may be carried out using a continuous liquid-liquid extraction or may be accomplished batchwise. The batch or continuous extraction can be repeated numerous times to enhance recovery. If liquid-liquid extraction is performed in a batchwise manner, examples of suitable systems include a stirred tank reactor, or a counter-current system such as an extraction column or a counter-currently configured CINC centrifugal extractor (commercially available from CINC, Carson City, Nev.). Preferably, the two phases should be contacted at a temperature greater than the melting point of the carboxylic acids such that the broth is fluid, preferably between about 0 C. and about 100° C., more preferably between about 70° C. and about 80° C., and even more preferably about 75° C. The two phases should be contacted for sufficient time to allow the concentration of carboxylic acid in each phase to reach equilibrium. Once equilibrium has been established, mixing is ceased, the phases are allowed to separate, and the extraction solvent phase is separated from the broth phase by any method known to those skilled in the art. The solvent may then be separated from the carboxylic acids by any suitable method known to those skilled in the art, e.g., evaporation, distillation, melt crystallization, or crystallization. Crystallization may be effected by sufficient cooling of the extraction solvent phase to precipitate dicarboxylic acids followed by filtration of resulting crystals. The latter may also serve as a method of purification by selectively isolating carboxylic acids which crystallize at higher temperatures while allowing carboxylic acids which crystallize at lower temperatures to remain in the filtrate, which may then be isolated by evaporation of the solvent.

The isolated carboxylic acids can be further purified by an additional crystallization step or by other means used by those skilled in the art such as distillation and chromatography methods. The recovered unsaturated carboxylic acids can then be hydrogenated to remove double bonds. The unsaturated carboxylic acids can also be further reacted with an oxidizing agent to oxidatively cleave the carbon-carbon double bonds to carboxyl groups to form a polycarboxylic acid. The oxidative cleavage of the carbon-carbon double bonds may be achieved with any oxidizing agent known in the art which will oxidatively cleave a carbon-carbon double bond to form two carboxyl groups. Such methods include, but are not limited to, reaction with ozone and subsequent oxidative work-up of the ozonides as described in U.S. Pat. No. 2,813,113, the entire contents of which are incorporated herein by reference; reaction with tungstic acid in the presence of hydrogen peroxide, preferably 60% hydrogen peroxide as described in WO 94/10122, the entire contents of which are incorporated herein by reference; reaction with chromic acid as described in U.S. Pat. No. 2,450,858, the entire contents of which are incorporated herein by reference; reaction with hypochlorite in the presence of ruthenium oxide as described in J. Am. Oil Chem. Soc., 54, 870A (1977), the entire contents of which are incorporated herein by reference; permanganate oxidation as described in J.Am. Oil Chem. Soc., 54 (858A) (1977), the entire contents of which are incorporated herein by reference; peroxyfornic acid oxidation as described in U.S. Pat. No. 5,380,928, the entire contents of which are incorporated herein by reference; cobalt bromide catalyzed peroxide oxidation as described in U.S. Pat. No. 4,606,863, the entire contents of which are incorporated herein by reference; cetylpyridinium chloride catalyzed phosphotungstic acid oxidation as described in JP 0183639, the contents of which are incorporated herein by reference.

In a particularly preferred embodiment, the extraction of the carboxylic acids from the fermentation broth can be carried out without adjusting the pH of the broth using at least one of the above-described extraction solvents.

In a particularly preferred embodiment, the isolated carboxylic acids are unsaturated and are then further processed utilizing methods including, but not limited to, hydrogenation to produce saturated carboxylic acids. Most preferably, hydrogenation is used to further process the resulting carboxylic acids. In general, the hydrogenation process involves drying the carboxylic acid crystals and charging them to a high pressure reactor along with a nickel or palladium on carbon catalyst. The contents of the reactor are agitated in a hydrogen atmosphere to a pressure ranging from about 400 to about 800 pounds per square inch, more preferably from about 500 to about 700 pounds per square inch, at a temperature ranging from about 160° C. to about 240° C., more preferably from about 200° C. to about 220° C., for a period of time ranging from about 2 to about 6 hours, more preferably from about 3 to about 5 hours. The contents of the reactor are then cooled to a temperature ranging from about 130° C. to about 180° C., more preferably from about 140° C. to about 160° C. The resulting hydrogenated carboxylic acid may then be further purified by distillation or crystallization.

Another preferred embodiment of the invention is based on the preparation of carboxylic acid by biooxidation of a crude mixture of oleic acid comprising a mixture of saturated and unsaturated carboxylic acids to form monocarboxylic and dicarboxylic acids, followed by extraction with a suitable extraction solvent as disclosed herein, recovery of the extracted carboxylic acids from the extractant by any conventional means, for example by recrystallization, followed by oxidation of the unsaturated carboxylic acid. While any crude mixture of oleic acid can be used, a particularly preferred crude mixture of oleic acid consists of the following % composition (GLC): 0.084 $C_{12}$, 2.148 $C_{14}$, 0.487 $C_{14:1}$; 0.190 $C_{15:1}$, 0.149 $C_{15:1}$, 4.458 $C_{16}$, 5.096 $C_{16:1}$, 0.150 $C_{17}$, 0.731 $C_{18}$, 71.21 $C_{18:1}$: 9.36 $C_{18:2}$, 0.513 $C_{18:3}$, 1.271 $C_{20:1}$, and 0.330 $C_{20:2}$.

Another preferred embodiment of the invention is based on the preparation of azelaic acid by biooxidation of oleic acid to form 9-octadecenedioic acid followed by oxidation of the 9-octadecenedioic acid to azelaic acid. While any grade of oleic acid can be used as the substrate, a typical technical grade oleic acid consists of the following carboxylic acids: 0.42% $C_{12}$; 2.7% $C_{14}$; 0.86% $C_{14:1}$, 6.3% $C_{16}$; 4.6% $C_{16:1}$, 0.93% $C_{17}$; 2.8% $C_{18}$; 71.8% $C_{18:1}$; 8.3% $C_{18:2}$; 0.58% $C_{18:3}$. The oleic acid can also be a high grade oleic acid obtained from a fatty oil of a Helianthus annuus (sunflower seed oil) species described, for example, in U.S. Pat. No. 4,627,192, the entire contents of which are incorporated herein by reference. Such oils are very rich in oleic acid and contain at least 80% by weight of oleic acid.

After the 9-octadecenedioic acid has been obtained by the biooxidation method disclosed herein, it can be recovered from the fermentation broth using the extraction method disclosed herein. pH adjustment of the broth is optional. The preferred pH range is from about 4.0 to about 6.0. The fermentation broth may be heated to about 70° C. to about 80° C. Heating the broth helps to reduce the viscosity to allow for better contact between the broth and the extractant. The broth is then contacted with the extraction solvent. The pH of the broth can be adjusted to reduce the amount of carboxylate salts present in the extract. The preferred means of contacting the broth with the extraction solvent is via a continuous liquid-liquid extraction. The 9-octadecenedioic acid is recovered from the extraction solvent by any standard means including, for example, recrystallization or evaporation.

After the 9-octadecenedioic acid has been obtained by the biooxidation and recovery methods disclosed herein, it may be reacted with ozone and further treated under oxidative conditions to yield azelaic acid. The mixed oxidation products are then further oxidized to azelaic acid as, for example, in the method disclosed in U.S. Pat. No. 5,420,316, the entire contents of which are incorporated by reference herein. A number of variations of the above azelaic acid preparation are contemplated for use with the present invention. For example, simple esters of oleic acid such as ethyl oleate, ethyl oleate, and the like can be used in place of the oleic acid in the production of 9-octadecenedioic acid as well as natural fats and oils having a relatively high oleic acid content.

The process described herein is superior when compared to techniques for isolating carboxylic acids from aqueous fermentation broth using saturated hydrocarbon, solvents such as hexane, cyclohexane, heptane, and octane due to the increased solubility and partition coefficient of a containing solvent containing one or more olefins. The processes are also superior to using solvents such as octanol, octanone, or other water insoluble ketones or alcohols. Although these alcohol and ketone solvents may have a greater extraction partition coefficient for the dicarbo-xylic acids, they also extract color containing impurities with the dicarboxylic acids, which are not as prevalent in olefin extracted carboxylic acids according to the present invention. Alcohol and ketone solvents do not crystallize the dicarboxylic acids on cooling the separated extract as in olefin extracts but rather form a two-phase system with an upper phase of solvent and a lower phase of carboxylic acids as residue phase that eventually becomes a solid with cooling. In addition, alcohol and ketone solvents have a greater solubility in water than do olefin-based extractants according to the present invention. This greater water solubility leads to increased processing for removal of water from the extract and the removal of solvent from extracted broth. Carboxylic acids isolated by extraction using solvents according to the present invention contain less carboxylic salts or soaps than those isolated using alcohol or ketone solvents. Olefin-based extraction solvents according to the present invention are also advantageous since they engender less emulsion formation during extraction than aromatic, alcohol and ketone solvents. The present extraction solvents are also superior to aromatic solvents such as toluene, xylenes, and other aromatic solvents since these aromatic solvents extract impurities leading to more color in the isolated diacids and are an environmental concern. Hydrogenation of the unsaturated carboxylic acids obtained by these processes results in saturated carboxylic acids that would be otherwise difficult to obtain.

The following examples are meant to illustrate but not to limit the scope of the invention.

EXAMPLES

The carboxylic acids listed below are abbreviated as follows in the following examples.

| Carboxylic Acid | Abbreviation |
| --- | --- |
| Myristic Acid | C14M |
| Myristoleic | C14:1M |
| Palmitic Acid | C16M |
| Palmitoleic Acid | C16:1M |
| Stearic Acid | C18M |
| Oleic Acid | C18:1M |
| Linoleic Acid | C18:2M |
| Tetradecanedioic Acid | C14D |
| Tetradecenedioic Acid | C14:1D |
| Pentadecanedioic Acid | C15D |
| Hexadecanedioic Acid | C16D |
| Hexadecenedioic Acid | C16:1D |
| Heptadecanedioic Acid | C17D |
| Heptadecenedioic Acid | C17:1D |
| Octadecanedioic Acid | C18 |
| Octadecenedioic Acid | C18:1D |
| Octadecdienedioic Acid | C18:2D |
| Eicosanedioic Acid | C20D |
| Eicosenedioic Acid | C20:1D |

Example 1

A fermentor was charged with a semi-synthetic growth medium having the composition 75 g/l glucose (annydrous), 6.7 g/l Yeast Nitrogen Base (Difco Laboratories), 3 g/l yeast extract, 3 g/l ammonium sulfate, 2 g/l monopotassium, phosphate, 0.5 g/l sodium chloride. Components were made as concentrated solutions for autoclaving then added to the fermentor upon cooling: final pH approximately 5.2. This charge was inoculated with 5–10% of an overnight culture of C. tropicalis HDC23-3 (see PCT/US99/20797) prepared in YM medium (Difco Laboratories) as described in the methods of Examples 17 and 20 of U.S. Pat. No. 5,254,466. Air and agitation were supplied to maintain the dissolved oxygen at greater than about 40% of saturation versus air. The pH was maintained at about 5.0 to 8.5 by the addition of 5N caustic soda on pH control. Both a fatty acid feedstream (commercial oleic acid in this example) having a typical composition: 2.4% $C_{14}$; 0.7% $C_{14:1}$; 4.6% $C_{16}$; 5.7% $C_{16:1}$; 5.7% $C_{17:1}$; 1.0% $C_{18}$; 69.9% $C_{18:1}$; 8.8% $C_{18:2}$; 0.30% $C_{18:3}$; 0.90% $C_{20:1}$; and a glucose cosubstrate feed were added in a feedbatch mode beginning near the end of exponential growth. Caustic was added on pH control during the bioconversion of fatty acids to diacids to maintain the pH in the desired range. Determination of fatty acid and diacid content was determined by a standard methyl ester protocol using gas liquid chromatography (GLC).

Example 2

A fermentor was charged with a medium consisting of 27 g/L glucose (from Corn Syrup), 4.9 g/L potassium phosphate, monobasic, 0.6 g/L magnesium sulfate, 0.5 g/L ammonium sulfate, 0.1 g/L calcium chloride, 0.05 g/L SAGS 471 antifoam, 0.067 g/L citric acid, 0.023 g/L ferric chloride, 0.012 mg/L biotin, 4.32 mg/L manganese sulfate, 0.07 mg/L cupric sulfate, 0.72 mg/L zinc sulfate, and water. Component concentrations are given as their anhydrous forms. These were heat sterilized in a suitable manner. The pH was adjusted to 5.8 with ammonia prior to the addition of a 3% inoculum of Candida tropicalis HDC 23-3. The culture was grown through exponential growth at 35° C. with ammonia added on pH control at pH 5.8. Near the end of exponential growth, conditions were changed to temperature 30° C. and pH control at 5.8 using 20% caustic soda. Two feedsteams, a substrate and a cosubstrate, were also started to initiate the conversion of the substrate fatty acids to dicarboxylic acids. The substrate feedstream was a mixture of 99.9% Emery® 244 Oleic acid and 0.1% Emery® 2301 methyl oleate comprising about 87.7% oleic acid, 4.4% linoleic acid, 3.2 steric acid, 3% palmitic acid, and minor amounts of other fatty acids ranging from C10 to C24 and was added to the fermentor as a series of periodic pulses. The cosubstrate feed was a 45% aqueous solution of glucose prepared using corn syrup fed continuously throughout the fermentation. The conversion was continued to accumulate diacids in the fermentation broth. The carboxylic acid composition of the broth was determined by gas chromatography and is set forth below in Table 1:

TABLE 1

| Component | Wt % by ISTD |
|---|---|
| C14:1M | .04 |
| C16M | .05 |
| C18M | .03 |
| C18:1M | .39 |
| C14D | .03 |
| C14:1D | .17 |
| C15D | .11 |
| C16D | .47 |
| C17D | .07 |
| C18D | .45 |
| C18:1D | 10.94 |
| C18:2D | .52 |
| Total | 13.27 |

2000 grams fermentation broth at pH 5.5, containing carboxylic acids was extracted 3 times; each time using a fresh 1448 g of a solvent made up of 10% tertiary-butyl acetate and 90% diisobutylene solvent by weight to effectively remove greater than about 90% of the dicarboxylic acids present. The extraction process was performed by combining the fermentation broth and solvent in a 3-neck 5 liter round bottom flask having a stopcock on the bottom of the flask, with an air condenser and mechanical stirrer attached. The mixture was heated with vigorous stirring to 77° C. After 10 minutes of stirring at 77° C., the heating and agitation were stopped and the phases allowed to separate and each isolated.

An additional 2000 grams of fermentation broth was extracted in the same manner described herein and the extractant solvent phases were combined.

The combined solvent phases were heated, while stirring, to 60° C. until all the carboxylic acids were completely dissolved. The mixture was then slowly cooled to 25° C. with stirring. The dicarboxylic acids crystallized, and the crystals were removed by filtration. The majority of solvent remaining in the filtercake was allowed to evaporate under ambient conditions and the residual solvent was then removed by reduced pressure, 29 inches of vacuum, and heat, 45° C. to give 440 grams of crystals.

Analysis of the crystals isolated by crystallization and filtration gave the following results:

Acid Value=350

Saponification Value=354

Transmittance as a 25% solution in DMSO at (440 nm/550 nm)=62/94

Melting Point=62–69° C.

The carboxylic acid composition of the crystals was determined by gas chromatography and is set forth below in Table 2.

TABLE 2

| Component | Wt % by ISTD |
|---|---|
| C14:1M | .03 |
| C16M | .03 |
| C18M | .05 |
| C18:1M | .47 |
| C18:2M | .03 |
| C12D | .07 |
| C14D | .12 |
| C14:1D | .47 |
| C15D | .10 |
| C16D | 3.23 |
| C16:1D | .11 |
| C17D | .06 |
| C17:1D | .17 |
| C18D | 3.74 |
| C18:1D | 80.79 |
| C18:2D | 2.29 |
| C20D | .18 |
| C20:1D | .19 |

Transmittance is the % transmittance of a 25% by weight solution of a material in A.C.S. spectophotometric grade methyl sulfoxide and measured in a 25 mm×105 mm round cuvette cell at 440 nm and 550 nm respectively that has been set to 100% transmittance using the methyl sulfoxide solvent. Methods for determining acid value, saponification value, iodine value and composition by gas chromatography can be found in the published Official Methods and Recommended Practices of the American Oil Chemists' Society; 5th ed. ISBN: 0-935315-97-7 AOCS Press, Champaign, Ill. (1998).

Example 3

170 grams of the dried carboxylic acid crystals obtained in Example 2, which were composed primarily of octadecenedioic acid, were added to 0.68 grams of 5% palladium on carbon #3610 containing 52% water obtained from Precious Metals Corporation and combined in a high pressure reactor. The contents of the reactor were agitated under a 600 pounds per square inch hydrogen atmosphere at 220° C. for 4 hours, then cooled to 150° C., and then removed. The final weight of the material was 170.6 grams. This hydrogenated material was then filtered to remove the palladium on carbon catalyst. Analysis of the material gave the following results:

Acid Value=345

Saponification Value=348

Transmittance as a 25% solution in DMSO at (440 nm/550 nm)=66/89 melting Point=120–123° C.

The carboxylic acid composition of the hydrogenated material was determined by Gas Chromatography and is set forth below in Table 3.

TABLE 3

| Component | Wt % by ISTD |
|---|---|
| C16M | .02 |
| C18M | .79 |
| C12D | .07 |
| C14D | .12 |
| C15D | .06 |
| C16D | 3.42 |
| C17D | .24 |

TABLE 3-continued

| Component | Wt % by ISTD |
|---|---|
| C18D | 89.23 |
| C20D | .42 |
| Total | 94.37 |

Distillation: 142.85 grams of distillate was recovered from 160.02 grams of the hydrogenated carboxylic acid. The distillate was collected from a vapor temperature of 220° C. at 0.17 mmHg to 242° C. at 0.18 mmHg. Analysis of the material gave the following results:

Acid Value=358
Saponification Value=358
Transmittance as a 25% solution in DMSO at (440 nm/550 nm)=94/99
Melting Point=122–124° C.

The carboxylic acid composition of the distillate was determined by Gas Chromatography and is set forth below in Table 4.

TABLE 4

| Component | Wt % by ISTD |
|---|---|
| C16M | .03 |
| C18M | .85 |
| C12D | .08 |
| C14D | .13 |
| C15D | .06 |
| C16D | 3.78 |
| C17D | .27 |
| C18D | 94.46 |
| C20D | .35 |
| Total | 100.01 |

Those with skill in the art will envision modifications of the various embodiments and examples described herein which are still considered to be within the scope of the invention. For example, notwithstanding examples directed to fermentation broth, it is contemplated that the extraction solvents described herein can be used to extract carboxylic acids from aqueous mixtures in general.

What is claimed is:

1. A method for isolating at least one unsaturated carboxylic acid from a fermentation broth comprising:
   providing a fermentation broth containing at least one carboxylic acid;
   contacting a solvent containing at least one olefin with the fermentation broth;
   allowing the at least one carboxylic acid to separate into the solvent;
   isolating the solvent containing the at least one carboxylic acid from the fermentation broth;
   separating the solvent from the at least one carboxylic acid; and
   hydrogenating the at least one carboxylic acid to produce a saturated carboxylic acid.

2. A method according to claim 1 wherein the at least one olefin solvent is selected from the group consisting of cyclohexene, 1-hexene, 1-octene, 1-decene, diisobutylene, nonene, alpha olefins having up to about 20 carbon atoms, and combinations thereof.

3. A method according to claim 1 wherein the solvent contains a cosolvent which increases the partition coefficient of the solvent as compared to the solvent without the cosolvent.

4. A method according to claim 3 wherein the cosolvent is selected from the group consisting of tertiary-butyl acetate, methyl isobutyl ketone, methyl tert-butyl ether, 2-octanol, 1-octanol, dodecanol, decanol, 2-octanone, 2-decanone and combinations thereof.

5. A method according to claim 3 wherein the solvent comprises tertiarybutyl acetate and diisobutylene.

6. A method according to claim 5 wherein a minor amount of the solvent is tertiarybutyl acetate and a major amount of the solvent is diisobutylene.

7. A method according to claim 6 wherein the solvent contains about 10% tertiarybutyl acetate and about 90% diisobutylene by weight.

8. A method according to claim 1 wherein the solvent is separated from the at least one carboxylic acid by a method selected from the group consisting of evaporation, crystallization and distillation.

9. A method according to claim 1 wherein the at least one carboxylic acid is hydrogenated by charging it in a high pressure reactor with a catalyst selected from the group consisting essentially of nickel on carbon and palladium on carbon.

10. A method according to claim 1 further comprising adjusting the viscosity of the fermentation broth.

11. A method according to claim 10 wherein the viscosity is adjusted by beating the fermentation broth.

12. A method according to claim 10 wherein the temperature of the fermentation broth is between about 0° C. and about 100° C.

13. A method according to claim 10 wherein the temperature is between about 70° C. and about 80° C.

14. A method according to claim 13 wherein the temperature is about 75° C.

15. A method according to claim 1 further comprising adjusting the pH of the fermentation broth.

16. The method according to claim 15 wherein the pH is between about 2.0 to about 7.0.

17. The method according to claim 16 wherein the pH is between about 3.0 to about 6.0.

18. The method according to claim 16 wherein the pH is about 5.0.

19. A method according to claim 1 wherein the at least one carboxylic acid is a dicarboxylic acid.

20. A method for isolating at least one unsaturated carboxylic acid from an aqueous mixture comprising:
   providing an aqueous mixture containing at least one carboxylic acid;
   contacting a solvent containing at least one olefin with the aqueous mixture;
   allowing the at least one carboxylic acid to separate into the solvent;
   isolating the solvent containing the at least one carboxylic acid from the
   aqueous mixture;
   separating the solvent from the at least one carboxylic acid; and
   hydrogenating the at least one carboxylic acid to produce a saturated carboxylic acid.

21. A method according to claim 20 wherein the at least one carboxylic acid is a dicarboxylic acid.

22. A method according to claim 20 wherein the at least one olefin solvent is selected from the group consisting of cyclohexene, 1-hexene, 1-octene, 1-decene, diisobutylene, nonene, alpha olefins having up to about 20 carbon atoms, and combinations thereof.

23. A method according to claim 20 wherein the solvent contains a cosolvent which increases the partition coefficient of the solvent as compared to the solvent without the cosolvent.

24. A method according to claim 23 wherein the cosolvent is selected from the group consisting of tertiary-butyl acetate, methyl isobutyl ketone, methyl tertbutyl ether, 2-octanol, 1-octanol, dodecanol, decanol, 2-octanone, 2-decanone and combinations thereof.

25. A method according to claim 23 wherein the solvent comprises tertiary butyl acetate and diisobutylene.

26. A method according to claim 25 wherein a minor amount of the solvent is tertiary butyl acetate and a major amount of the solvent is diisobutylene.

27. A method according to claim 26 wherein the solvent contains about 10% tertiary butyl acetate and about 90% diisobutylene by weight.

28. A method according to claim 20 wherein the solvent is separated from the at least one carboxylic acid by a method selected from the group consisting of evaporation, crystallization and distillation.

29. A method according to claim 20 wherein the at least one carboxylic acid is hydrogenated by charging it in a high pressure reactor with a catalyst selected from the group consisting essentially of nickel on carbon and palladium on carbon.

30. A method according to claim 20 further comprising adjusting the viscosity of the aqueous mixture.

31. A method according to claim 30 wherein the viscosity is adjusted by heating the aqueous mixture.

32. A method according to claim 30 wherein the temperature of the aqueous mixture is between about 0° C. and about 100° C.

33. A method according to claim 32 wherein the temperature is between about 70° C. and about 80° C.

34. The method according to claim 32 wherein the temperature is about 75° C.

35. The method according to claim 20 further comprising adjusting the pH of the aqueous mixture.

36. The method according to claim 20 wherein the pH is between about 2.0 to about 7.0.

37. The method according to claim 36 wherein the pH is between about 3.0 to about 6.0.

38. The method according to claim 36 wherein the pH is about 5.0.

* * * * *